(12) United States Patent
Crooks et al.

(10) Patent No.: US 8,101,779 B2
(45) Date of Patent: Jan. 24, 2012

(54) ENANTIOSELECTIVE SYNTHESIS OF (+) AND (−)-2-[1-(2,6-DICHLOROPHENOXY)-ETHYL]-1,3-DIAZACYCLOPENT-2-ENE

(75) Inventors: Peter A. Crooks, Nicholasville, KY (US); Ashish Pramod Vartak, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 12/574,578

(22) Filed: Oct. 6, 2009

(65) Prior Publication Data

US 2010/0087657 A1   Apr. 8, 2010

Related U.S. Application Data

(60) Provisional application No. 61/195,309, filed on Oct. 6, 2008.

(51) Int. Cl.
*C07D 233/22* (2006.01)
(52) U.S. Cl. .................................................. 548/353.1
(58) Field of Classification Search ................ 548/353.1
See application file for complete search history.

(56) References Cited

U.S. PATENT DOCUMENTS 4,518,783 A * 5/1985 Biedermann et al. ...... 548/353.1

FOREIGN PATENT DOCUMENTS

WO   WO 2010/016844 A1 *   2/2010

OTHER PUBLICATIONS

Biedermann et al., "Two Stereoisomeric Imidazoline Derivatives: Synthesis and Optical and $\alpha_2$- Adrenoceptor Activities," Journal of Medicinal Chemistry, 1986, pp. 1183-1188, vol. 29, No. 7.
Akhurst, "Lofexidine in Opiate Withdrawal: A Safety and Usage Survey," Pharmacoepidemiology and Drug Safety, 2000, pp. 43-47, vol. 9, No. 1.
Wilkins et al., "Lofexidine and Clonidine in Moderate Essential Hypertension," Clinical Pharmacology and Therapeutics, 1981, pp. 752-757, vol. 30, No. 6.
Wilffert et al., "Interference of Enantiomers of Lofexidine with $\alpha$-Adrenoceptors," International Archives of Pharmacology, 1985, pp. 18-32, vol. 273, No. 1.
Crassous et al., "$\alpha_2$-Adrenoreceptors Profile Modulation.3.[1](R)-(+)-$m$-Nitrobiphenyline, a New Efficient and $\alpha_{2C}$-Subtype Selective Agonist," Journal of Medicinal Chemistry, 2007, pp. 3964-3968, vol. 50, No. 16.

* cited by examiner

*Primary Examiner* — Shawquia Young
(74) *Attorney, Agent, or Firm* — Crowell & Moring LLP

(57) ABSTRACT

Methods for the enantioselective synthesis of (+) and (−) lofexidine or 2-[1-(2,6)-dichlorophenoxy)-ethyl]-1,3-diazacyclopent-2-ene involve converting (+) or (−) 1-methyl-1-[2,6-dichlorophenoxy]ethanamide to an (+) or (−) imino-ether intermediate by electrophilic attack of the amide oxygen by a trimethoxonium ion and, without isolation, converting the (+) or (−) imino-ether intermediate to (+) or (−) 2-[1-(2,6-dichlorophenoxy)-ethyl]1,3-diazacyclopent-2-ene by adding ethylene diamine; and optionally converting the (+) or (−) 2-[1-(2,6-dichlorophenoxy)-ethyl]1,3-diazacyclopent-2-ene into a pharmaceutically acceptable acid addition salt thereof.

21 Claims, No Drawings

ENANTIOSELECTIVE SYNTHESIS OF (+) AND (−)-2-[1-(2,6-DICHLOROPHENOXY)-ETHYL]-1,3-DIAZACYCLOPENT-2-ENE

CROSS-REFERENCE TO RELATED APPLICATIONS

This application claims priority under 35 U.S.C. §119 to U.S. Provisional Application No. 61/195,309, filed on Oct. 6, 2008, the entire content of which is hereby incorporated by reference in its entirety.

TECHNICAL FIELD

This application provides a method for the enantioselective synthesis of (+) and (−) lofexidine or 2-[1-(2,6)-dichlorophenoxy)-ethyl]-1,3-diazacyclopent-2-ene.

BACKGROUND OF THE INVENTION (±)-lofexidine (1), an imidazoline with $\alpha_2$-adrenergic agonist properties is clinically utilized for the purpose of ameliorating symptoms of disorders that stem from abberations in the $\alpha_2$-adrenoreceptor function. For example, (±)-lofexidine has been used as an anti-hypertensive and for treating the physical and psychological symptoms of opiate abstinence in opiate-addicts (Wilkins, et al., *Clin. Pharmacol. Ther.* 1981, 30, 752-757; and Akhurst, *Pharmacoepidemiology and Drug Safety* 2000, 9, 43-47).

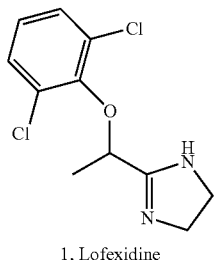
1, Lofexidine

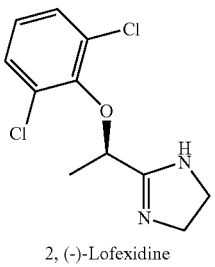
2, (−)-Lofexidine

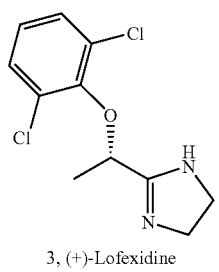
3, (+)-Lofexidine

The pharmacological properties of (±)-lofexidine are evident upon the interaction of lofexidine either with $\alpha_2$ adrenergic receptors or with any other macromolecule. These pharmacological properties are the result of the individual properties of its two enantiomeric forms, (+)-lofexidine (2) and (−)-lofexidine (3). These chemically distinct entities differ in their affinities toward $\alpha_2$-adrenergic receptors. (−)-lofexidine shows about a 10-fold higher affinity than that of (+)-lofexidine when both are individually pitted against the known $\alpha_2$-adrenergic ligand, $^3$[H]-clonidine, for competitive displacement from the receptor. This difference between (+)-lofexidine and (−)-lofexidine is mirrored in their unequal capacity to lower mean arterial blood pressure; the effect of (+)-lofexidine is apparent at doses as low as 561 ng/kg, while that of (−)-lofexidine is not seen even at doses as high as 10 μg/kg (Wilffert, et al., *Arch. Int. de. Pharmcodynamie et de Ther.* 1985, 273, 18-32). (±)-lofexidine is useful in the treatment of hypertension, as well as in the treatment of withdrawal symptoms in opiate addicts. Accordingly, the enantioselective synthesis and usage of solely (−)-lofexidine has been attempted. Three distinct approaches toward the synthesis of (−)-lofexidine are well known, and are described below.

Optical resolution of (±)-lofexidine into (+)-lofexidine and (−)-lofexidine. In the work of Biedermann et. al., (+) and (−)-dibenzoyl tartaric acids are reacted with (±)-lofexidine and subsequently allowed to crystallize from acetone (Biedermann et al., *J. Med. Chem.* 1986, 29, 1183-1188). After a total of 4 recrystallizations, optically pure (+)-lofexidine is obtained (where (+)-tartaric acid is employed) and (−)-lofexidine is obtained (where (−)-tartaric acid is employed). However, the overall yield of this resolution process is typically 5-10%, making this methodology impractical for large scale preparation.

Enantioselective approach toward (+)-lofexidine and (−)-lofexidine based on amide dehydration, nitrile alcoholysis and imidazoline formation: Another approach described in the work of Biedermann et. al. employs chirally pure ethyl lactate as a starting material. The synthesis (Scheme 1) involves a two-step inversion of the α-chiral center of ethyl lactate followed by amidation, dehydration of the amide, alcoholysis of the resulting nitrile and conversion of the resulting imino-ether into imidazoline followed by salification by anhydrous HCl. An overall yield of 5% is obtained after 8 synthetic transformations that employ two high-vacuum distillation processes.

Scheme 1. Biedermann's first approach toward enantiopure lofexidine.
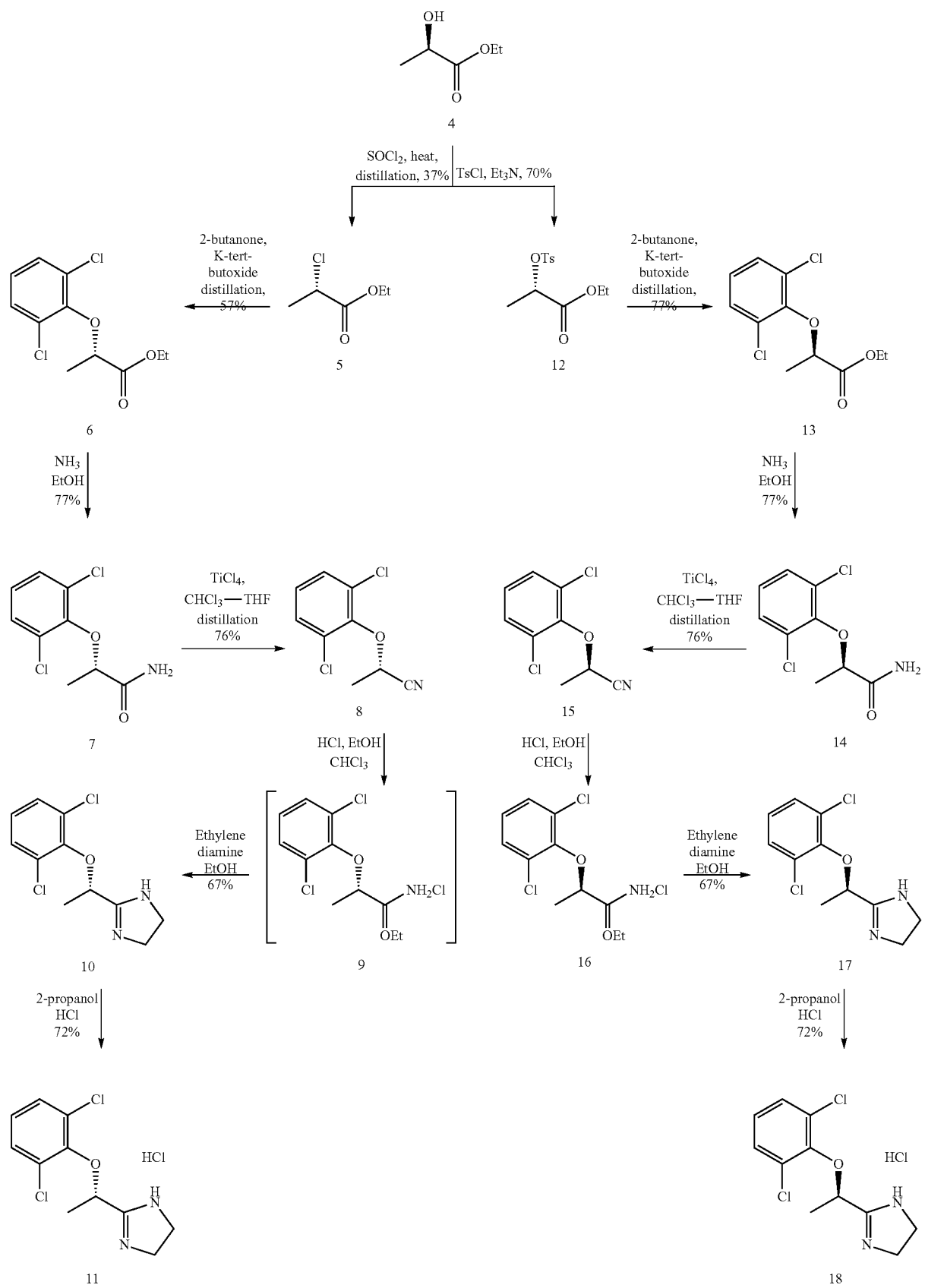

Enantioselective approach toward (+)-lofexidine and (−)-lofexidine based on Lewis-acid mediated imidazoline formation: U.S. Pat. No. 4,518,783 is directed to a synthetic route toward chirally pure lofexidine (Scheme 2) that begins from intermediate 6 of scheme 1. Amidation with ethylene diamine is followed by Lewis-acid mediated cyclization to imidazoline. An overall yield of 4% is obtained over 5 synthetic transformations that involve a silica-gel column chromatography process following the Lewis-acid mediated imidazoline formation.

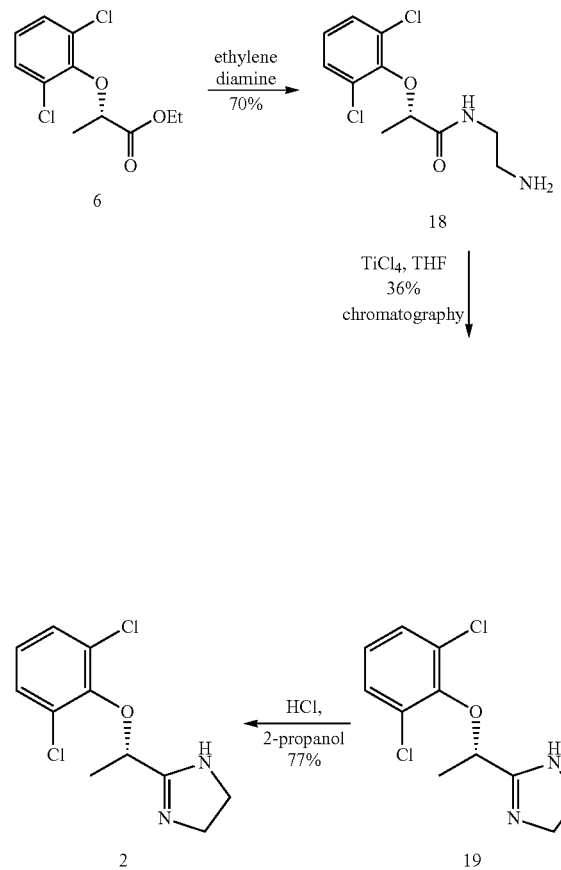

The synthesis of a related imidazoline; m-nitrobiphenyline, is also known. (Crassous et al., *J. Med. Chem.* 2007, 50, 3964-3968). Shown in Scheme 3, a Mitsonubu inversion of the α-hydroxy function of methyl lactate yields an analog of 6. The resulting substituted methyl ester 20 is converted to an imidazoline by heating it with ethylene diamine in dry toluene in the presence of AlCl₃. This approach fails to yield a chirally pure product, as the enantiomeric excess was found to be 72%.

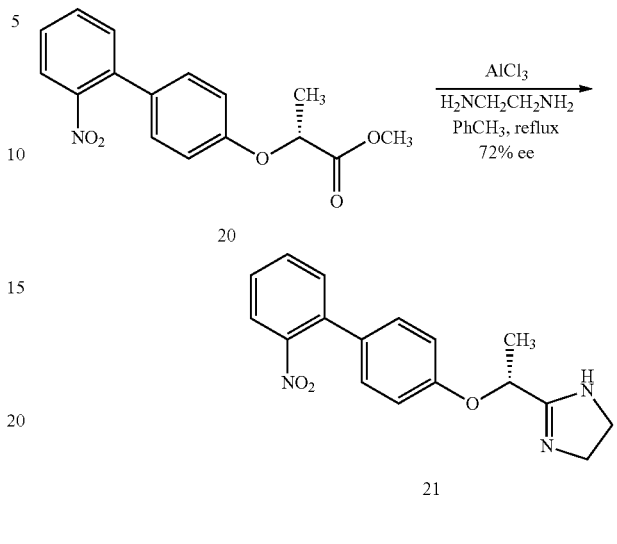

Thus, new methods for synthesizing (+) and (−) lofexidine are needed, which provide greater yields than the processes known in the art, and which improve the ease and improves the overall ease and yields of the process, without harm to the stereochemical integrity of the product.

SUMMARY OF THE INVENTION

This invention relates to the chemical transformation of chirally pure methyl lactate to yield chirally pure (+)-lofexidine or (−)-lofexidine with better yield than known methods, and without the usage of additional purification techniques, such as distillation or chromatography.

One aspect of the present invention provides an enantioselective synthesis of (+) or (−) 2-[1-(2,6-dichlorophenoxy)-ethyl]1,3-diazacyclopent-2-ene (lofexidine) or a pharmaceutically acceptable acid addition salt thereof comprising: converting (+) or (−) 1-methyl-1-[2,6-dichlorophenoxy]ethanamide to the (+) or (−) imino-ether intermediate by electrophilic attack of the amide oxygen by a trimethoxonium ion and, without isolation, converting the (+) or (−) imino-ether intermediate to (+) or (−) 2-[1-(2,6-dichlorophenoxy)-ethyl] 1,3-diazacyclopent-2-ene by adding ethylene diamine. Optionally, (+) or (−) 2-[1-(2,6-dichlorophenoxy)-ethyl]1,3-diazacyclopent-2-ene may be converted into a pharmaceutically acceptable acid addition salt thereof.

Another aspect of the present invention provides an enantioselective synthesis of (+) or (−) 2-[1-(2,6-dichlorophenoxy)-ethyl]1,3-diazacyclopent-2-ene or a pharmaceutically acceptable acid addition salt thereof comprising: (a) converting (+) or (−) 1-methyl-1-hydroxyethanoate to (+) or (−) 1-methyl-1-[2,6-dichlorophenoxy]ethanoate by reacting with 2,6-dichlorophenol, triphenylphosphine and diisopropyl azodicarboxylate; (b) converting the (+) or (−) 1-methyl-1-[2,6-dichlorophenoxy]ethanoate to (+) or (−) 1-methyl-1-[2,6-dichlorophenoxy]ethanamide; (c) converting (+) or (−) 1-methyl-1-[2,6-dichlorophenoxy]ethanamide to (+) or (−) imino-ether intermediate by electrophilic attack of the amide oxygen by a trimethoxonium ion and, without isolation, converting the (+) or (−) imino-ether intermediate to (+) or (−) 2-[1-(2,6-dichlorophenoxy)-ethyl]1,3-diazacyclopent-2-ene by adding ethylene diamine; and (d) optionally converting the (+) or (−) 2-[1-(2,6-dichlorophenoxy)-ethyl]1,3-diazacyclopent-2-ene into a pharmaceutically acceptable acid addition salt thereof.

DETAILED DESCRIPTION OF THE INVENTION

Definitions and Abbreviations

In accordance with this detailed description, the following abbreviations and definitions apply. It must be noted that as used herein, the singular forms "a", "an", and "the" include plural referents unless the context clearly dictates otherwise. Thus, for example, reference to "an antibody" includes a plurality of such antibodies and reference to "the dosage" includes reference to one or more dosages and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

By the term "subject" or "patient" as used herein is meant to include a mammal. The mammal can be a canine, feline, primate, bovine, ovine, porcine, camelid, caprine, rodent, or equine. Preferably the mammal is human.

By the term "optionally" is meant that the step or action is not required or mandatory, but may or may not be performed.

The following abbreviations are used herein:

| | |
|---|---|
| $AlCl_3$ | aluminum chloride |
| $CDCl_3$ | deuterated chloroform |
| $CH_2Cl_2$ | dichloromethane |
| DIAD | diisopropyl azodicarboxylate |
| EtOH | ethanol |
| HCl | hydrochloric acid |
| i-PrOH | isopropyl alcohol |
| $K_2CO_3$ | potassium carbonate |
| $Na_2SO_4$ | sodium sulfate |
| NMR | nuclear magnetic resonance |
| $Ph_3P$ | triphenylphosphine |

The present invention provides the first instance of an enantioselective synthesis of lofexidine that proceeds in meaningful overall yields and does not require additional purification techniques, such as distillation or column chromatography.

While all previous procedures have utilized a two-step amide-dehydration and nitrile alcoholysis to generate an imino-ether intermediate, the present method involves a one step conversion. The present methods utilize a direct electrophilic attack of the amide oxygen by a trimethoxonium ion. This transformation greatly improves the overall ease and yield of the process, without harm to the stereochemical integrity of the configuration about the α-carbon.

The present synthesis scheme provides chirally pure lofexidine with greater yields than schemes known in the art. In one embodiment, the enantioselective syntheses of the present invention provide an overall yield of chirally pure lofexidine or a pharmaceutically acceptable acid addition salt thereof of at least 50%. In another embodiment, the enantioselective syntheses of the present invention provide an overall yield of chirally pure lofexidine or a pharmaceutically acceptable acid addition salt thereof of at least 60%. In a specific embodiment, the overall yield of chirally pure lofexidine, or a pharmaceutically acceptable acid addition salt thereof, is at least 64%.

The present invention provides an enantioselective synthesis of (+) or (−) lofexidine or a pharmaceutically acceptable acid addition salt thereof which comprises converting (+) or (−) 1-methyl-1-[2,6-dichlorophenoxy]ethanamide to the (+) or (−) imino-ether intermediate by electrophilic attack of the amide oxygen by a trimethoxonium ion. Then, without isolation, the (+) or (−) imino-ether intermediate is converted to (+) or (−) lofexidine by adding ethylene diamine. The (+) or (−) lofexidine can be converted into a pharmaceutically acceptable acid addition salt if desired. The syntheses of the present invention are described in detail below.

Commercially available (+) or (−) methyl lactate (22 or 23) (for example, obtained from Sigma Aldrich) may serve as starting materials in the present synthesis. The synthesis of (−)-lofexidine (3), beginning from 22 is illustrated and described below.

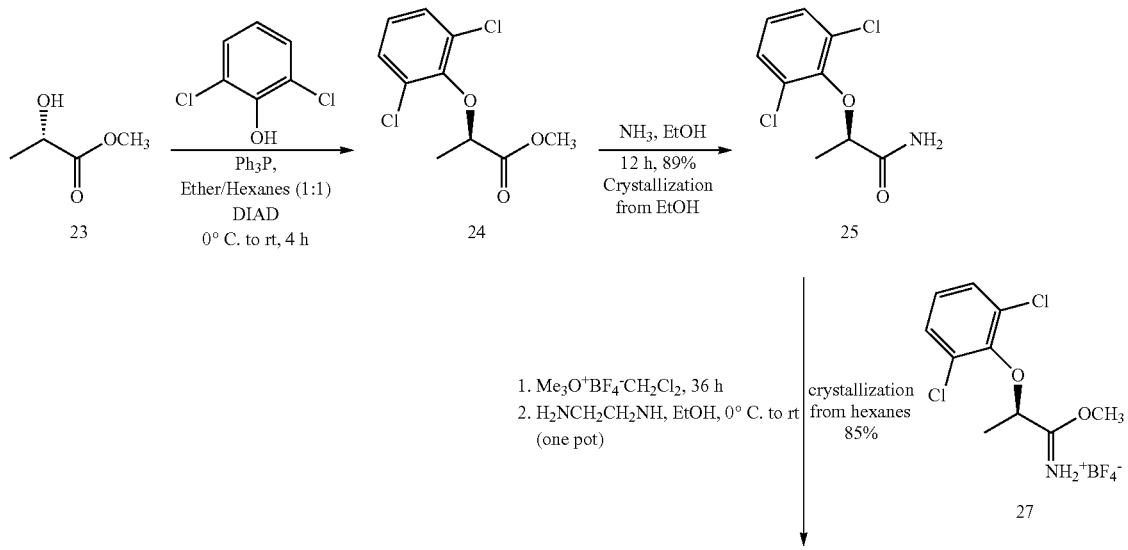

Scheme 4. Synthesis of (−)-lofexidine (3).

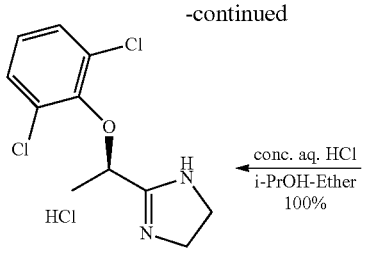

64% overall yield
100% ee

26 conc. aq. HCl
i-PrOH-Ether
100%

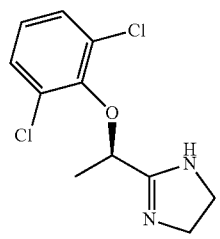

3

The starting material, commercially available (+) or (−) methyl lactate ((+) or (−) 1-methyl-1-hydroxyethanoate), is reacted with 2,6-dichlorophenol, triphenylphosphine ($Ph_3P$) and diisopropyl azodicarboxylate (DIAD) to provide (+) or (−) 1-methyl-1-[2,6-dichlorophenoxy]ethanoate. In one embodiment, the reaction takes place in a solvent that dissolves the (+) or (−) 1-methyl-1-hydroxyethanoate, 2,6-dichlorophenol, triphenylphosphine and diisopropyl azodicarboxylate and precipitates triphenylphosphine oxide. The solvent can consist of an approximately 1:1 ratio of a polar aprotic solvent and a nonpolar solvent. In one embodiment, the polar aprotic solvent is ether, and the nonpolar solvent is hexanes. In one embodiment, the (+) or (−) 1-methyl-1-hydroxyethanoate is reacted with 2,6-dichlorophenol, triphenylphosphine and diisopropyl azodicarboxylate at approximately 0° C. and then allowed to warm to approximately room temperature.

For example, methyl ester 22 is reacted with 2,6-dichlorophenol, triphenylphosphine and diisopropyl azodicarboxylate in a solvent consisting of ether and hexanes in a 1:1 ratio at 0° C. and the reaction mixture is allowed to warm to room temperature over a period of four hours. This particular solvent combination allows for complete dissolution of all starting materials and initiation of the precipitation of triphenylphosphine oxide from the reaction mixture. The utilization of anhydrous grades of these solvents during the preparation of 24 is not necessary, in contrast to what generally is used for this type of transformation. After completion of the reaction (about 4 hours), the precipitation of triphenylphosphine is completed by dilution of the reaction mixture with heptane to twice its volume. After filtration, the filtrate is evaporated to an amber oil (crude 24) which is subjected to the next step without any further purification, in this specific example.

Next, the (+) or (−) 1-methyl-1-[2,6-dichlorophenoxy] ethanoate is converted to (+) or (−) 1-methyl-1-[2,6-dichlorophenoxy]ethanamide. Conversion of the ether to the amide can be accomplished by treatment with ammonia. In one embodiment, the (+) or (−) 1-methyl-1-[2,6-dichlorophenoxy]ethanoate is converted to the amide by treatment with a solution of ammonia in an alcohol. For example, crude 24 is treated with a solution of ammonia in absolute ethanol for 12 hours to provide partial crystallization of the product 25 from the reaction mixture. The reaction is then refluxed to drive off excess ammonia and diluted with boiling ethanol to dissolve the entirety of the solid mass. Undissolved solids are then filtered to provide a clear, pale yellow filtrate that yields large needles of pure 25 upon cooling to 0° C.

Then, the (+) or (−) 1-methyl-1-[2,6-dichlorophenoxy] ethanamide is converted to (+) or (−) imino-ether intermediate by electrophilic attack of the amide oxygen by a trimethoxonium ion and, without isolation, converting the (+) or (−) imino-ether intermediate to (+) or (−) 2-[1-(2,6-dichlorophenoxy)-ethyl]1,3-diazacyclopent-2-ene by adding ethylene diamine. In one embodiment, the trimethoxonium ion is trimethyloxonium tetrafluoroborate. In one embodiment, approximately 1.1 equivalents ethylene diamine are added as an alcohol solution.

For example, pure 25 obtained above is dissolved in reagent-grade $CH_2Cl_2$ and treated with an equivalent of trimethyloxonium tetrafluoroborate. The suspension becomes a clear solution upon stirring for 36 hours at room temperature. This solution, containing an imino-ether intermediate, is cooled to 0° C. and 1.1 equivalents of ethylene diamine are added as a 10% solution in absolute ethanol. Upon warming to room temperature, the turbid mixture is evaporated to dryness and partitioned between $CH_2Cl_2$ and 5% aqueous $K_2CO_3$. The organic layer is dried and then evaporated, which provides a solid residue that yields (−)-lofexidine (3) as a mass of fine white needles when crystallized from hexanes. This material is chemically and optically pure, as judged from its NMR spectra and optical rotation values.

The resulting (+) or (−) 2-[1-(2,6-dichlorophenoxy)-ethyl] 1,3-diazacyclopent-2-ene (lofexidine) product can be converted into a pharmaceutically acceptable acid addition salt thereof if desired. For example, to provide the HCl salt, the crystalline material (3) is dissolved in a 4:1 mixture of ether and i-PrOH and is treated with 1.2 equiv. of aqueous conc. HCl. This results in precipitation of very fine colorless needles that are recovered by filtration and dried in air.

The present invention's conversion to the HCl salt advantageously uses aqueous HCl rather than anhydrous HCl as taught in the literature. The use of the 4:1 mixture of ether and i-PrOH and with 1.2 equiv. of aqueous conc. HCl allows for the precipitation of a microcrystalline hydrochloride salt of 3, compound 26. The solvents and their ratios are tailored to achieve this precipitation. The use of anhydrous HCl in i-PrOH, as known in the literature, is tedious to use on large scales and generally produces a voluminous precipitate of the salt.

Compound 2, the enantiomer of (+)-lofexidine (2) and its hydrochloride salt may be obtained in a similar fashion, starting with the (+)-methyl lactate (23).

Although the present invention has been described in detail with reference to the example below, it is understood that various modifications can be made without departing from the spirit of the invention, and would be readily known to the skilled artisan.

EXAMPLE (−)-2-(2,6-dichlorophenoxy)-propionamide (25). To 1-L round bottom flask equipped with a stir-bar were added (+)-methyl lactate (25.00 g, 240.26 mmol), $Ph_3P$ (63.00 g, 241 mmol), and 2,6-dichlorophenol (39.16 g, 240.26 mmol) and ether-hexanes (1:1, 250 mL). After cooling to 0° C., DIAD (49.00 g, 241 mmol) was added dropwise over 30 minutes and the resulting yellow solution was warmed to room temperature over a period of 4 hours, during which, fine white needles of triphenyl phosphine oxide crystallized. The mixture was diluted with 250 mL of heptanes, stirred for 30 minutes and filtered through a Buchner funnel. The filter cake was washed with heptane (100 mL, 2×) and the filtrates were evaporated to an amber oil containing 24, that was directly subjected to the next transformation without any further purification.

The amber oil obtained above (65 g crude) was dissolved in 500 mL absolute EtOH and cooled to 0° C. Ammonia gas was passed through this solution until the solution was judged to be saturated (seen as greatly increased bubbling of gas). The mixture was allowed to warm to room temperature (unstirred) over 12 h, following which, it was refluxed for 15 min. and diluted with EtOH (250 mL) and refluxed for 30 min. This mixture was filtered hot and the filtrate was cooled in the refrigerator for 2 h which led to the formation of a mass of white needles, that was removed by filtration and dried in air for 30 min to yield 25 (50.00 g, 89%). $^1$H NMR (300 MHz, CDCl$_3$) δ ppm 7.35-7.25 (m, 2H, Ar), 7.03 (t, J=8.4 Hz, 1H, Ar), 6.93 (br, s, NH), 6.08 (br, s, NH), 4.93 (q, 1H, J=6.9 Hz), 1.50 (d, 3H, J=6.9 Hz); $^{13}$C NMR (75 MHz, CDCl$_3$) δ ppm 174.2, 148.9, 129.7, 129.4, 125.7, 79.3, 18.1; mp=192-193° C. (EtOH); $[\alpha]^{23}_D$=−18.9° (c 1.0, EtOH) (lit.$^4$ $[\alpha]^{20}_D$=−20.1° (c 1.0, acetone).

(−)-2-[1-(2,6-dichlorophenoxy)-ethyl]-1,3-diazacyclopent-2-ene (3). A mixture of 25 (25 g, 106.8 mmol), trimethyloxonium tetrafluoroborate (16.6 g, 110 mmol) and CH$_2$Cl$_2$ (600 mL) was stirred for 36 hours, during which the coarse suspension changed to a clear, colorless solution. Cooling of this solution of 0° C. was followed by a dropwise addition of ethylene diamine (7.00 g, 1.1 equiv) over 10 minutes. The resulting solution was warmed to room temperature, diluted with absolute ethanol (200 mL) and then evaporated to dryness. The pasty white residue was partitioned between 5% aqueous K$_2$CO$_3$ (200 mL) and CH$_2$Cl$_2$ (500 mL). The organic layer was dried (Na$_2$SO$_4$) and evaporated under reduced pressure. Recrystallization of the residue from boiling hexanes (500 mL) afforded pure 3 as white needles that were removed by filtration and dried in air (23.52 g, 85%). $^1$H NMR (300 MHz, d$_6$-DMSO) δ ppm 7.46-7.44 (m, 2H, Ar), 7.14 (t, J=7.8 Hz, 1H, Ar), 6.45 (s, 1H, NH), 4.79 (q, J=6.6 Hz, 1H), 3.43-3.37 (s, br, 4H), 1.47 (d, J=6.6 Hz, 3H). $^{13}$C NMR (75 MHz, d$_6$-DMSO) δ ppm 166.3, 150.0, 130.0, 129.6, 129.5, 129.2, 126.6, 77.3, 50.4 (very broad), 19.2; mp=129-130° C. (hexanes); $[\alpha]^{23}_D$=−80.2° (c 1.0, EtOH) (lit.$^4$ $[\alpha]^{20}_D$=−76.4° (c 1.0, EtOH).

(−)-2-[1-(2,6-dichlorophenoxy)-ethyl]-1,3-diazacyclopent-2-ene hydrochloride (26). To a solution of 3 (10.00 g, 39 mmol) in 4:1 ether/i-PrOH (100 mL) was added dropwise conc. aqueous HCl (3.5 mL, 1.1 equiv.). Upon stirring for 10 minutes the suspension was diluted with ether (100 mL), filtered and the filter-cake was washed with ether (3×50 mL) and air-dried, affording 26 (11.40 g, 100%). $^1$H NMR (300 MHz, d$_6$-DMSO) δ ppm 10.86 (s, 2H, NH), 7.52 (d, J=8.1 Hz, 2H, Ar), 7.23 (t, J=8.1 Hz, 1H, Ar), 5.20 (q, J=6.6 Hz, 1H) 3.87 (s, br, 4H), 1.66 (d, J=6.6 Hz, 3H); $^{13}$C NMR (75 MHz, d$_6$-DMSO) δ ppm 169.5, 149.2, 130.3, 129.1, 127.5, 73.9, 45.2, 19.5; mp=226-227° C.; $[\alpha]^{23}_D$=−39.0° (c 1.0, EtOH) (lit.$^5$ $[\alpha]^{20}_D$ −34.5° (c 1.0, EtOH).

All references cited above are incorporated herein in their entirety for all purposes.

That which is claimed:

1. An enantioselective synthesis of (+) or (−) 2-[1-(2,6-dichlorophenoxy)-ethyl]1,3-diazacyclopent-2-ene or a pharmaceutically acceptable acid addition salt thereof comprising:
converting (+) or (−) 1-methyl-1-[2,6-dichlorophenoxy]ethanamide to an (+) or (−) imino-ether intermediate by electrophilic attack of the amide oxygen by a trimethoxonium ion and, without isolation, converting the (+) or (−) imino-ether intermediate to (+) or (−) 2-[1-(2,6-dichlorophenoxy)-ethyl]1,3-diazacyclopent-2-ene by adding ethylene diamine; and optionally converting the (+) or (−) 2-[1-(2,6-dichlorophenoxy)-ethyl]1,3-diazacyclopent-2-ene into a pharmaceutically acceptable acid addition salt thereof.

2. The enantioselective synthesis of claim 1 wherein the trimethoxonium ion is trimethyloxonium tetrafluoroborate.

3. The enantioselective synthesis of claim 1 wherein approximately 1.1 equivalents ethylene diamine are added as an alcohol solution.

4. The enantioselective synthesis of claim 1 wherein the (+) or (−) 2-[1-(2,6-dichlorophenoxy)-ethyl]1,3-diazacyclopent-2-ene is crystallized from hexanes.

5. The enantioselective synthesis of claim 1 wherein the (+) or (−) 2-[1-(2,6-dichlorophenoxy)-ethyl]1,3-diazacyclopent-2-ene is converted into a HCl salt by dissolving and treating with aqueous concentrated HCl.

6. The enantioselective synthesis of claim 5 wherein the (+) or (−) 2-[1-(2,6-dichlorophenoxy)-ethyl]1,3-diazacyclopent-2-ene is converted into a HCl salt by dissolving in an approximately 4:1 mixture of ether and isopropyl alcohol and treating with aqueous concentrated HCl to precipitate a microcrystalline hydrochloride salt of (+) or (−) 2-[1-(2,6-dichlorophenoxy)-ethyl]1,3-diazacyclopent-2-ene.

7. The enantioselective synthesis of claim 1, wherein the synthesis provides an overall yield of (+) or (−) 2-[1-(2,6-dichlorophenoxy)-ethyl]1,3-diazacyclopent-2-ene or a pharmaceutically acceptable acid addition salt thereof of at least 50%.

8. The enantioselective synthesis of claim 1, wherein the synthesis provides an overall yield of (+) or (−) 2-[1-(2,6-dichlorophenoxy)-ethyl]1,3-diazacyclopent-2-ene or a pharmaceutically acceptable acid addition salt thereof of at least 60%.

9. An enantioselective synthesis of (+) or (−) 2-[1-(2,6-dichlorophenoxy)-ethyl]1,3-diazacyclopent-2-ene or a pharmaceutically acceptable acid addition salt thereof comprising:
(a) converting (+) or (−) 1-methyl-1-hydroxyethanoate to (+) or (−) 1-methyl-1-[2,6-dichlorophenoxy]ethanoate by reacting with 2,6-dichlorophenol, triphenylphosphine and diisopropyl azodicarboxylate;
(b) converting the (+) or (−) 1-methyl-1-[2,6-dichlorophenoxy]ethanoate to (+) or (−) 1-methyl-1-[2,6-dichlorophenoxy]ethanamide;
(c) converting (+) or (−) 1-methyl-1-[2,6-dichlorophenoxy]ethanamide to (+) or (−) imino-ether intermediate by electrophilic attack of the amide oxygen by a trimethoxonium ion and without isolation converting the (+) or (−) imino-ether intermediate to (+) or (−) 2-[1-(2,6-dichlorophenoxy)-ethyl]1,3-diazacyclopent-2-ene by adding ethylene diamine; and
(d) optionally converting the (+) or (−) 2-[1-(2,6-dichlorophenoxy)-ethyl]1,3-diazacyclopent-2-ene into a pharmaceutically acceptable acid addition salt thereof.

10. The enantioselective synthesis of claim 9 wherein step (a) is performed in a solvent that dissolves the (+) or (−) 1-methyl-1-hydroxyethanoate, 2,6-dichlorophenol, triphenylphosphine and diisopropyl azodicarboxylate and precipitates triphenylphosphine oxide.

11. The enantioselective synthesis of claim 9 wherein step (a) is performed in a solvent consisting of an approximately 1:1 ratio of a polor aprotic solvent and a nonpolar solvent.

12. The enantioselective synthesis of claim 9 wherein step (a) is performed in a solvent consisting of an approximately 1:1 ratio of ether and hexanes.

13. The enantioselective synthesis of claim 9 wherein in step (a) the (+) or (−) 1-methyl-1-hydroxyethanoate is reacted with 2,6-dichlorophenol, triphenylphosphine and diisopropyl azodicarboxylate at approximately 0° C. and allowed to warm to approximately room temperature.

14. The enantioselective synthesis of claim 9 wherein the (+) or (−) 1-methyl-1-[2,6-dichlorophenoxy]ethanoate is converted to (+) or (−) 1-methyl-1-[2,6-dichlorophenoxy]ethanamide by treatment of a solution of ammonia in an alcohol.

15. The enantioselective synthesis of claim 9 wherein the trimethoxonium ion is trimethyloxonium tetrafluoroborate.

16. The enantioselective synthesis of claim 9 wherein in step (c) approximately 1.1 equivalents ethylene diamine are added as an alcohol solution.

17. The enantioselective synthesis of claim 9 wherein the (+) or (−) 2-[1-(2,6-dichlorophenoxy)-ethyl]1,3-diazacyclopent-2-ene is crystallized from hexanes.

18. The enantioselective synthesis of claim 9 wherein the (+) or (−) 2-[1-(2,6-dichlorophenoxy)-ethyl]1,3-diazacyclopent-2-ene is converted into a HCl salt by dissolving and treating with aqueous concentrated HCl.

19. The enantioselective synthesis of claim 18 wherein the (+) or (−) 2-[1-(2,6-dichlorophenoxy)-ethyl]1,3-diazacyclopent-2-ene is converted into a HCl salt by dissolving in an approximately 4:1 mixture of ether and isopropyl alcohol and treating with aqueous concentrated HCl to precipitate a microcrystalline hydrochloride salt of (+) or (−) 2-[1-(2,6-dichlorophenoxy)-ethyl]1,3-diazacyclopent-2-ene.

20. The enantioselective synthesis of claim 9, wherein the synthesis provides an overall yield of (+) or (−) 2-[1-(2,6-dichlorophenoxy)-ethyl]1,3-diazacyclopent-2-ene or a pharmaceutically acceptable acid addition salt thereof of at least 50%.

21. The enantioselective synthesis of claim 9, wherein the synthesis provides an overall yield of (+) or (−) 2-[1-(2,6-dichlorophenoxy)-ethyl]1,3-diazacyclopent-2-ene or a pharmaceutically acceptable acid addition salt thereof of at least 60%.

* * * * *